(12) United States Patent
Peng

(10) Patent No.: US 11,769,253 B2
(45) Date of Patent: Sep. 26, 2023

(54) METHOD AND SYSTEM FOR SELECTING A REGION OF INTEREST IN AN IMAGE

(71) Applicant: StraxCorp Pty. Ltd., Melbourne (AU)

(72) Inventor: Yu Peng, Melbourne (AU)

(73) Assignee: CURVEBEAM AI LIMITED, Melbourne (AU)

( * ) Notice: Subject to any disclaimer, the term of this patent is extended or adjusted under 35 U.S.C. 154(b) by 0 days.

(21) Appl. No.: 17/518,858

(22) Filed: Nov. 4, 2021

(65) Prior Publication Data
US 2022/0058418 A1 Feb. 24, 2022

Related U.S. Application Data

(63) Continuation of application No. 16/448,285, filed on Jun. 21, 2019, now Pat. No. 11,170,245.

(51) Int. Cl.
*G06T 7/00* (2017.01)
*G06T 7/11* (2017.01)
(Continued)

(52) U.S. Cl.
CPC .......... *G06T 7/0012* (2013.01); *G06T 5/002* (2013.01); *G06T 5/009* (2013.01); *G06T 5/40* (2013.01);
(Continued)

(58) Field of Classification Search
None
See application file for complete search history.

(56) References Cited

U.S. PATENT DOCUMENTS 6,175,655 B1 1/2001 George, III et al.
8,958,614 B2 2/2015 Zhan et al.
(Continued)

FOREIGN PATENT DOCUMENTS

WO WO 2013/183051 A1 12/2013

OTHER PUBLICATIONS

Australian Examination Report for Application No. 2019204372, dated Aug. 2, 2019.
(Continued)

*Primary Examiner* — Vikkram Bali
(74) *Attorney, Agent, or Firm* — NIXON PEABODY LLP; Jeffrey L. Costellia

(57) ABSTRACT

A system and computer-implemented method for analysing or monitoring a subject, the method comprising: identifying one or more objects of interest that have been segmented from a first image comprising any of a baseline scan, a follow-up scan or a reference image of the subject; identifying predefined landmarks of the objects; determining reference morphometries pertaining to the objects by performing morphometrics on the objects by reference to the landmarks; selecting one or more regions of interest (ROIs) from the objects according to the reference morphometries, comprising identifying respective locations of the ROIs relative to the reference morphometries; performing a first analysis of the one or more ROIs; performing at least one corresponding second analysis of the one or more ROIs in respectively at least one second image comprising any other of a baseline scan, a follow-up scan or a reference image; and generating a comparison of one or more results of the first analysis and one or more corresponding results of the second analysis.

20 Claims, 8 Drawing Sheets
(2 of 8 Drawing Sheet(s) Filed in Color)

(51) Int. Cl.
    *G06T 7/70*         (2017.01)
    *G06T 5/00*         (2006.01)
    *G06T 5/40*         (2006.01)
    *G06T 7/60*         (2017.01)

(52) U.S. Cl.
    CPC .................. *G06T 7/11* (2017.01); *G06T 7/60* (2013.01); *G06T 7/70* (2017.01); *G06T 2207/20036* (2013.01); *G06T 2207/20081* (2013.01); *G06T 2207/20084* (2013.01); *G06V 2201/03* (2022.01)

(56) References Cited

U.S. PATENT DOCUMENTS

| | | |
|---|---|---|
| 9,373,173 B2 | 6/2016 | Weistrand |
| 2009/0226060 A1 | 9/2009 | Gering et al. |
| 2009/0316975 A1 | 12/2009 | Kunz et al. |
| 2013/0223704 A1 | 8/2013 | Lay et al. |
| 2013/0336553 A1 | 12/2013 | Buisseret et al. |
| 2015/0178918 A1 | 6/2015 | Arnaud et al. |
| 2016/0063720 A1 | 3/2016 | Han et al. |
| 2017/0330319 A1 | 11/2017 | Xu et al. |

OTHER PUBLICATIONS

Burrows et al., "Assessing Bone Microstructure at the Distal Radius in Children and Adolescents Using HR-pQCT: A Methological Pilot Study", Journal of Clinical Densitometry: Assessment of Skeletal Health, Humana Press, Totowa, NJ, US, vol. 13, No. 4, Oct. 2020, pp. 451-455.

Lang et al., "Volumetric Quantitative Computed Tomography of the Proximal Femur: Precision and Relation to Bone Strength", Bone, vol. 21, No. 1, Mar. 17, 1997, pp. 101-108.

Extended European Search Report (Application No. 20177179.7) dated Oct. 29, 2020.

METHOD AND SYSTEM FOR SELECTING A REGION OF INTEREST IN AN IMAGE

RELATED APPLICATION

This application is based on and claims the benefit of the filing and priority dates of U.S. patent application Ser. No. 16/448,285 filed 21 Jun. 2019, the content of which as filed is incorporated herein by reference.

FIELD OF THE INVENTION

The present invention relates to a method and system for selecting a two- or three-dimensional region of interest in an image, of particular but by no means exclusive application in applying artificial intelligence to the analysis of medical images, such as for morphometric measurement. The region of interest may be a 2D region or 3D volume in such medical images. Possible medical imaging applications include Computed Tomography (CT), Magnetic Resonance (MR), Ultrasound, and Pathology Scanner imaging.

BACKGROUND

A region of interest (ROI) relates to a definition of the borders of an object or part of an object under consideration, typically as that object (or part object) appears in an image, and is a concept commonly used in medical imaging applications. The ROI in a medical image is selected or identified for analysis or assessment. For example, the boundaries of a tumour may be defined on a mammography scan as the ROI, such as to measure the tumour's size; the endocardial border may be identified on a coronary CT calcium scan as the ROI, perhaps during different phases of the cardiac cycle, for example, end-systole and end-diastole, for the purpose of assessing cardiac function; the femur neck may be identified as the ROI on a hip DXA scan for calculating the bone mineral density; the distal radius bone ROI may be selected on a wrist CT scan for assessing bone microstructure.

The selection of the ROI is important in medical image analysis, so that the clinically relevant region is identified for clinical analysis. For example, the distal region of a radius bone may be selected for bone microstructure assessment; inappropriate region selection can lead to an invalid assessment of bone microstructure. If a ROI is selected that is too proximal, the region will include too little trabecular tissue; if a ROI is selected that is too distal, the region will include too thin a cortex.

Also, in some diagnostic analyses, quantitative analysis of selected ROI needs to be compared to the reference values, which are calculated from large data samples. Inaccurate ROI selection makes such a comparison invalid. Precise region of interest selection in medical imaging is required for monitoring a disease or a treatment. If the ROI's selection is not precise and reproducible, different ROIs of the same patient during different visits will be analysed and compared, and the efficacy of a treatment regime may be compromised.

A ROI may be selected manually or semi-manually. The manual methods require the operators to draw contours of a ROI based on predefined rules. For example, U.S. Pat. No. 7,609,817 describes a method of selecting a femoral neck from hip images in bone densitometry. That patent discloses a femoral neck box, with a width and length of 1.5 cm×5.0 cm, centred on a new coordinate system with its width (1.5 cm) parallel to an x-axis (or femoral midline). The user may move the femoral neck box along and perpendicular to the femoral midline and is instructed to place the corner of the femoral neck box against the bone edge of the greater trochanter. Further, the user is instructed to reduce the width of the femoral neck box if the femoral neck is very short.

Some known systems include semi-manual ROI selection. Such semi-manual methods usually require the operator to give some initial input, based on which the ROI is identified and selected. For example, XtremeCT (™) (a high resolution peripheral quantitative computed tomography system provided by Scanco Medical AG, of Brüttisellen, Switzerland) requires operators to select a ROI to be scanned. The operator first acquires a 2D anterior-posterior projection of the proximal limb. On the 2D projection image, the operator visually identifies an anatomic landmark and manually intersects it with a horizontal reference line. From the reference line, the anatomic volume to be scanned is offset by a standard distance.

However, both manual and semi-manual methods are labour intensive and tedious, and ROI selection varies within and between operators. The variability in ROI selection is of great concern in cross-sectional or observational multicentre studies, and when pooling cross-sectional datasets for retrospective analyses (where multiple operators may have been involved in data collection). Moreover, selecting an ROI based on heuristic rules is another problem: ROI selection for assessment should include consideration of clinical implications, but heuristic rules-based selection may produce inferior clinical easement. For example, as described above, the femoral neck is defined as a fixed size box and the volume of the wrist to be scanned is selected based on a fixed distance. Either femoral neck or distal wrist volume selection is used to characterize an individual patient's skeletal status. Human femur bones vary in size, hence so do femoral necks. A fixed-size box can include other musculoskeletal material, such as muscle or adipose tissue, in patients with small femur bones, while covering only part of the femoral neck for patients with big femur bones. The wrist volume to be scanned is selected by a fixed distance from an anatomic landmark. However, bone morphology can vary markedly along the bone axis. Hence, in these techniques, comparisons between the microstructure assessments of patients with different bone length will commonly lead to no clinically helpful conclusion.

Another existing method of ROI selection involves co-registration. For example, one voxel-based morphometry method of brain MRI data involves firstly spatially normalizing all the subjects' scans to the same stereotactic space. This includes registering each of the images of the same template image by minimizing the residual sum of squared differences between them. The grey matter (corresponding to the ROI) is then selected from the normalized images; smoothing is applied, and finally a statistical analysis is performed to localize the group differences. This method selects a ROI with a consideration of brain morphometry. However, this method is mainly used in the group comparison studies; it is rarely used for single subjects, because registering every brain scan to the same template will remove the differences in brain anatomy among people.

Registration is also used to improve the ROI selection prevision during patient monitoring. The analysis of identical ROIs between repeated CT scans is important in monitoring changes in bone microarchitecture. In longitudinal studies, 3D registration is used to select the same ROI; this involves rotating and translating follow-up scans (such as second and third scans) to the coordinates of the first scan (or reference image). The registration procedure can select the ROIs of baseline and follow-up scans precisely for the same subject. However, in most diagnostic analysis, the measurement of the patient is compared to reference data calculated from a large population. The registration method cannot solve the problem of sub-optimal ROI selection between different subjects.

SUMMARY

According to a first aspect of the invention, there is provided a computer-implemented method for selecting one or more regions of interest (ROIs) in an image, the method comprising:

identifying predefined landmarks of the objects;
determining reference morphometries pertaining to the objects by performing morphometrics on the objects by reference to the landmarks;
selecting one or more ROIs from the objects according to the reference morphometries, comprising identifying respective locations of the ROIs relative to the reference morphometries; and
outputting the selected one or more ROIs.
wherein determining the reference morphometries comprises determining a shape, a size, or a shape and a size, of the one or more objects.

In an embodiment, performing the reference morphometrics further comprises measuring basic morphometries by performing basic morphometrics on the objects by reference to the detected landmarks and determining the reference morphometries based on the measured basic morphometries. For example, performing the reference morphometrics may comprise employing one or more trained deep learning reference morphometric models.

In an embodiment, the selecting of the one or more ROIs from the objects according to the reference morphometries further comprises determining the shapes and sizes of the respective ROIs.

In an embodiment, the method further comprises segmenting the objects from the image. In an example, segmenting the objects comprises generating masks of the respective segmented objects. Segmenting the objects may employ one or more trained machine learning segmentation models. In an example, the method comprises performing a plurality of segmentations.

In an embodiment, the method further comprises preparing the image for segmentation by pre-processing the image. For example, pre-processing the image may comprise applying a Gaussian blur function to the image to reduce noise, and/or applying histogram equalization to enhance contrast of the image.

In an embodiment, the method further comprises normalizing the objects before performing the reference morphometrics on the objects, such as from an image coordinate system into an anatomical coordinate system. For example, normalizing the objects may comprise coordinate transformation.

In an embodiment, the method may further comprise determining density of one or more of the selected ROIs using attenuation of a referent material (comprising, for example, an adjacent tissue such as muscle or fat, or a calibration phantom).

According to a second aspect of the invention, there is provided a system for selecting one or more regions of interest (ROIs) in an image, the system comprising:

an object and landmark identifier configured to identify one or more objects of interest that have been segmented from the image, and to identify predefined landmarks of the objects;
a morphometer configured to determine reference morphometries pertaining to the objects by performing morphometrics on the objects by reference to the landmarks;
a region selector configured to select one or more ROIs from the objects according to the reference morphometries, comprising identifying respective locations of the ROIs and determining respective shapes and sizes of the ROIs relative to the reference morphometries; and
a results output configured to output the selected ROIs.
wherein determining the reference morphometries comprises determining a shape, a size, or a shape and a size, of the one or more objects.

In an embodiment, the morphometer is configured to perform the reference morphometrics by measuring basic morphometries by performing basic morphometrics on the objects by reference to the detected landmarks and determining the reference morphometries based on the measured basic morphometries. For example, the morphometer may be further configured to perform the reference morphometrics by employing one or more trained deep learning reference morphometric models.

In an embodiment, the region selector is further configured to determine the shapes and sizes of the respective ROIs relative to the reference morphometries.

In an embodiment, the system further comprises a segmenter configured to segment the objects from the image. In an example, the segmenter is further configured generate masks of the respective segmented objects. The segmenter may employ one or more trained machine learning segmentation models to segment the objects.

In an embodiment, the system further comprises an image pre-processor configured to prepare the image for segmentation by pre-processing the image. In an example, the pre-processor is configured to reduce noise by applying a Gaussian blur function to the image, and/or to enhance contrast of the image by applying histogram equalization to the image.

In an embodiment, the system further comprises a normalizer configured to normalize the objects before reference morphometrics are performed on the objects, such as from an image coordinate system into an anatomical coordinate system. In one example, the normalizer normalizes the objects by coordinate transformation.

In an embodiment, the system further comprises a density determiner configured to determine density of one or more of the selected ROIs using attenuation of a referent material.

According to a third aspect of the invention, there is provided a computer program, comprising program code configured to, when executed by one or more processors, implement the method for selecting a region of interest (ROI) in an image of the first aspect. This aspect also provides a computer-readable medium, comprising such a computer program.

It should be noted that any of the various individual features of each of the above aspects of the invention, and any of the various individual features of the embodiments described herein including in the claims, can be combined as suitable and desired.

DRAWINGS

This patent or application file contains at least one drawing executed in color. Copies of this patent or patent application publication with color drawings(s) will be provided by the Office upon request and payment of the necessary fee.

In order that the invention may be more clearly ascertained, embodiments will now be described by way of example with reference to the following drawing, in which.

DETAILED DESCRIPTION

System

Figure 1:
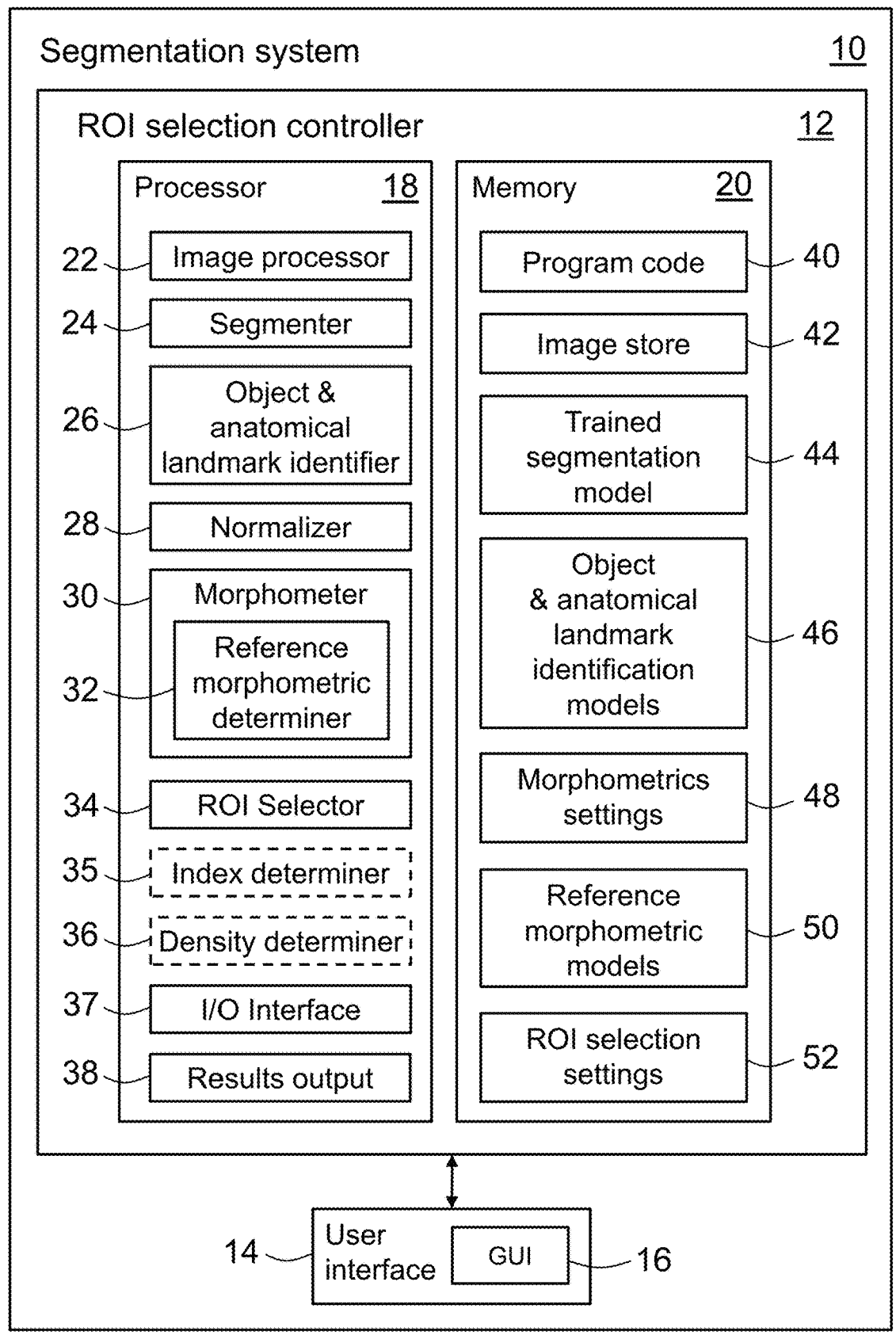
FIG. 1 is a schematic view of a segmentation system, according to an embodiment of the present invention.

FIG. 1 is a schematic view of a segmentation system 10 according to an embodiment of the present invention.

Referring to FIG. 1, system 10 comprises an ROI ('region of interest') selection controller 12 and a user interface 14 (including a GUI 16). User interface 14 typically comprises one or more displays (on one or more of which may be displayed the GUI 16), a keyboard and a mouse, and optionally a printer. ROI selection controller 12 includes at least one processor 18 and a memory 20. System 10 may be implemented, for example, as a combination of software and hardware on a computer (such as a personal computer or mobile computing device), or as a dedicated ROI selection system. System 10 may optionally be distributed; for example, some or all of the components of memory 20 may be located remotely from processor 18; user interface 14 may be located remotely from memory 20 and/or from processor 18.

Memory 20 is in data communication with processor 18, and typically comprises both volatile and non-volatile memory (and may include more than one of each type of memory), including RAM (Random Access Memory), ROM and one or more mass storage devices.

As is discussed in greater detail below, processor 18 includes an image processor 22, a segmenter 24, an object and anatomical landmarks identifier 26, a normalizer 28, a morphometer 30 (which includes a reference morphometric determiner 32), an ROI (region of interest) selector 34, an optional index determiner 35, an optional density determiner 36, an I/O interface 37 and a results output 38. Memory 20 includes program code 40, image store 42, trained segmentation model 44, object and anatomical landmark identification models 46, morphometrics settings 48, reference morphometric models 50, and ROI selection settings 52. ROI selection controller 12 is implemented, at least in part, by processor 18 executing program code 40 from memory 20.

In broad terms, I/O interface 37 is configured to read medical images into image store 42 of memory 20 for processing. Once system 10 has completed processing, I/O interface 37 outputs the result to, for example, results output 38 and/or to GUI 16. For example, I/O interface 37 may read CT scans in DICOM format into image store 42. After processor 18 has processed the scans, the selected ROI or ROIs may be outputted, such as by being presented to a user, stored, or used for further analysis (or a combination of any of these).

Image processor 22 of processor 18 is configured to process images before segmentation. For example, processor 18 can remove noise in the input images or enhance the contrast of the input images. Processor 18 can also process images after segmentation. For example, processor 18 can process segmented objects to make subsequent morphometrics easier.

Segmenter 24 performs segmentation using trained segmentation model 44 which, in this embodiment, employs artificial intelligence—that is, machine learning algorithms such as a deep learning neural network. For different applications, different models are trained. For example, for segmenting a brain image from one or more MRI scans, segmentation model 44 may have been trained using deep convolutional neural networks with MRI scans as training data. Such training would involve experts annotating the brains on the scans; for segmenting radius bone from wrist CT scans, segmentation model 44 may have been trained using deep convolutional neural networks with annotated wrist CT scans as training data.

Morphometer 30 measures the objects according to morphometrics settings 48. For different objects, different morphometrics are measured—the appropriate settings in each case being stored as morphometrics settings 48. For example, the required morphometrics measurements of radius bone are different from those required for measurements of the femur bone. For the same object but a different ROI selection, different morphometrics measurements are required. For example, for femoral troch region selection from the hip DXA scan, only the neck axis and shaft axis need be measured; for femoral neck selection, femoral head centre and the femoral head tangent plane may also need to be measured.

ROI selector 34 selects an ROI from the segmented objects according to the morphometrics measurements and ROI selection settings 52. For example, for selecting the femoral neck from a hip DXA scan, femoral neck box height may be defined as various percentages of the hip axis length for different study purposes.

System Workflow

Figure 2:
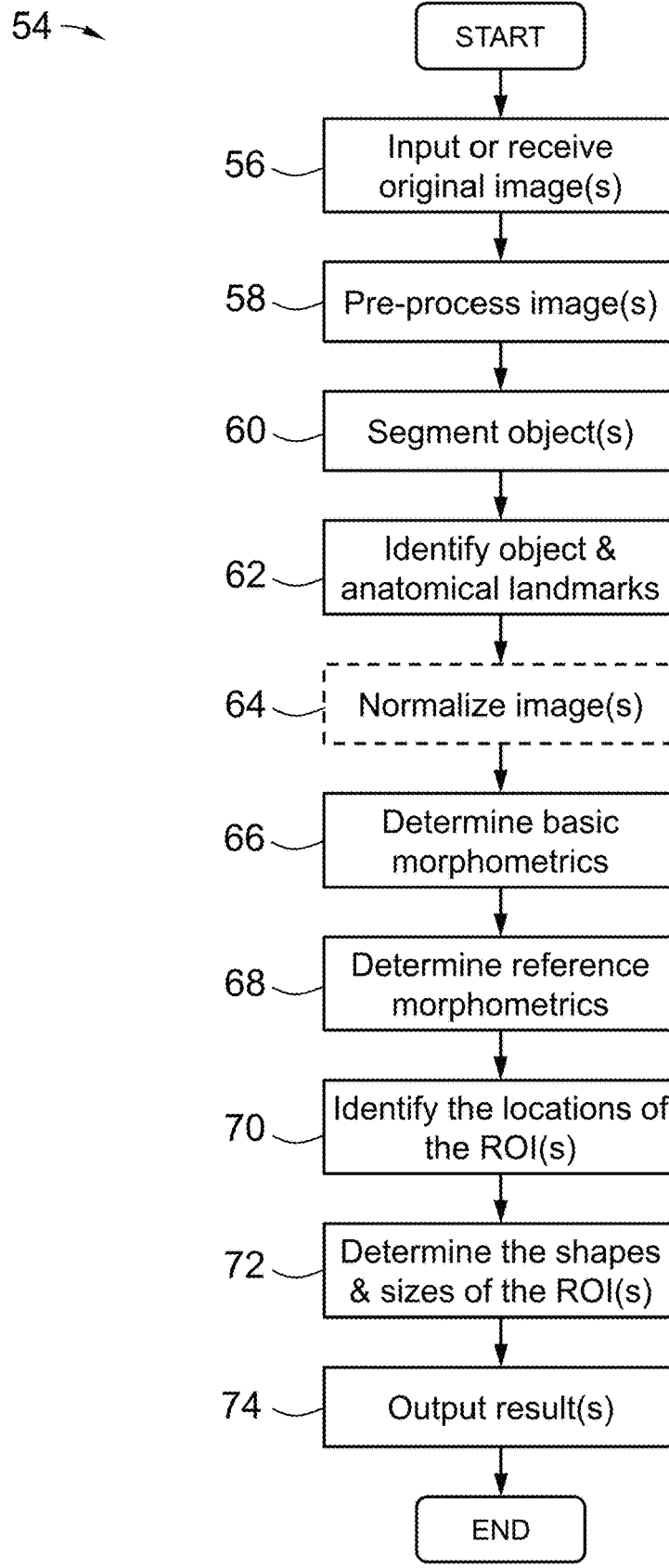
FIG. 2 is a schematic workflow of the operation of the segmentation system of FIG. 1, according to an embodiment of the present invention.

FIG. 2 depicts schematically the general workflow 54 of system 10. Referring to FIG. 2, in step 56, original images (such as in DICOM, TIFF or PNG format) are read into memory 20 of system 10. Memory 20 is preferably configured to allow high-speed access of data by system 10. For example, if system 10 is implemented as a combination of software and hardware on a computer (such as a personal computer), and the images may be read into RAM of memory 20.

At step 58, image processor 22 pre-processes the loaded images if required or desired. This prepares the images for the segmentation, so as to improve the results of segmentation (including to make those results satisfy a desired quality threshold). For example, the pre-processing may include applying a Gaussian blur function to an image to reduce noise, or include applying histogram equalization to enhance image contrast, or both.

At step 60, segmenter 24 segments objects of interest from the images, including—if desired—generating a mask of the segmented object. In this embodiment, segmentation model 44 is generally used for segmentation. For different objects, different machine learning models are trained. For example, different models are trained for segmenting brain from MRI scan and segmenting radius bone from wrist CT scan, respectively. Machine learning such as deep learning models are used to achieve accurate segmentation. However, in other embodiments, objects of interest are alternatively segmented using more conventional image processing algorithms, such as contour detection or blob detection, which in some applications may be acceptably accurate.

Furthermore, this step may include more than one segmentation (such as segmenting bone material from surrounding soft tissue, then segmenting one or more particular bones from the bone material). In such instances, different segmentation techniques may be employed in each segmentation, such as a pre-trained segmentation model 44 in the first segmentation and more conventional image processing method in the second segmentation (or vice versa), or two pre-trained segmentation models (one for each of the segmentation steps).

At step 62, the object or objects of interest, obtained by segmentation, and then relevant anatomical landmarks of the objects, are recognized and identified by object and anatomical landmarks identifier 26. For example, if segmenter 24 has segmented—from surrounding material in the image—the radius and ulna at this step the radius bone will be recognized and identified, then—for example—the radial head, styloid process, and ulnar notch will be recognized and identified. The identified anatomical landmarks will be later used for morphometric measurement.

The objects and anatomical landmarks are identified by pre-trained deep learning models, stored in object and anatomical landmark identification models 46.

At step 64 (which is optional in this embodiment), normalizer 28 normalizes segmented objects to facilitate subsequent morphometrics. Normalization typically comprises coordinate transformation, especially for 3D scans. Objects are segmented from images that are presented in an image coordinate system, while morphometrics are performed with respect to—for example—the anatomy. Thus, in the example of anatomy, transforming objects in the image coordinate system into the anatomical coordinate system simplifies morphometrics.

Next, the morphometrics themselves are conducted, as the automatic ROI selection is performed by referring to one or more clinically relevant morphometrics—referred to herein as reference morphometrics. While in some other cases the reference morphometrics can be measured directly, generally they are measured after segmentation and landmark detection.

For example, in a DXA hip scan, the hip length constitutes one reference morphometric, calculated from some basic morphometrics, which themselves are determined by referring to the detected landmarks. The calculation itself can be performed by any suitable (including conventional) image processing algorithm.

In another example, radius length is the reference morphometric, to which the ROI selector refers to select a bone volume for bone microstructure analysis. The radius length cannot be measured directly, as scanning the whole forearm is generally not feasible (owing to what would be an excessive radiation dose). Therefore, the basic morphometrics, such as the distal breadth, the diameter of mid-shaft, maximum distal head diameter and minimum distal head diameter, are first measured. In this embodiment, a deep learning model—pre-trained to predict the radius length on the basis of the aforementioned basic morphometrics—determines the radius length.

Thus, at step 66, morphometer 30 determines basic morphometrics for the one or more segmented and identified objects, according to morphometrics settings 48. For different objects and different requirements of ROI selection, different basic morphometrics are determined. Morphometer 30 is configured to implement image processing so as to make such measurements. Morphometer 30 measures the desired basic morphometrics, such as of tangent line of femoral head, the neck axis, and the hip end line, by reference to the anatomical landmarks that were identified in step 62 by object and anatomical landmarks identifier 26. For example, for femoral neck ROI selection from a hip DXA image, morphometer 30 would employ anatomical landmarks such as the femoral head tangent, femoral head centre, neck axis and shaft axis.

Some reference morphometrics may, in some applications, be measured directly. For example, if the radius distal breadth is chosen as the reference morphometric, it may be measured directly by referring to detected landmarks. In such situations, morphometer 30 measures the required one or more reference morphometrics, without requiring the use of reference morphometric determiner. That is, the reference morphometric are the basic morphometrics.

However, this is generally not so, so in most cases the reference morphometrics are calculated based on the basic morphometrics by reference morphometric determiner 32. This is done at step 68. For example, in a hip DXA scan, reference morphometric determiner 32 may calculate the hip length by constructing a line between the vertex point of the femoral head and centre point of the last slice of shaft bone (both points having been identified in step 66), then calculating the line's length. The line construction may be performed using any suitable image processing algorithm.

Reference morphometric determiner 32 of this embodiment, however, has the ability to determine reference morphometrics using one or more pre-trained deep learning reference morphometric models 50. As discussed above, a deep learning reference morphometric model may be trained to predict (in this example) the radius bone length based on the measurements of distal breadth, diameter of mid-shaft, maximum distal head diameter and minimum distal head diameter (being basic morphometrics measured in step 66). Hence, reference morphometric determiner 32 of this embodiment can determine the radius bone length (the reference morphometric in that example) using this deep learning reference morphometric model 50, based on an analysis of the distal portion only of the subject's forearm.

Next, ROI selector 34 selects one or more ROIs from the objects for respective purposes, according to the ROI selection settings 52 and the reference morphometrics calculated at step 68. ROI selector 34 performs ROI selection in two steps: at step 70, ROI selector 34 identifies the location of each respective ROI, and at step 72, ROI selector 34 determines the shape and size of the respective ROIs (whether in two- or three-dimensions). For example, for distal radius region selection, ROI selector 34 first identifies the location of the ROI as a percentage of the radius bone length from the radius distal tip, and ROI selector 34 then defines the thickness of the selected volume as another percentage of the radius bone length.

At step 74, the results, comprising the selected ROI or ROIs, are outputted. This may entail passing these results to results output 38 for outputting to, for example, a user (for presentation to the user via, for example, a monitor of user interface 14). Alternatively, this may entail passing these results to another system (such as via I/O interface 37). In still a further alternative, this entails using the results as the input of further analysis, such as by the optional index determiner 35 or density determiner 36 (or both). Combinations of any of these are also envisaged.

Index determiner 35 is configured to use segmenter to segment the selected ROI(s) into different structures, and to calculate characterizing indices that characterize these structures. For example, after the selection of a bone volume ROI from a CT wrist scan, index determiner 35 might control segmenter 24 to further segment the selected ROI into cortex, transitional region, and trabecular region, then calculate indices (such as trabecular architecture and porosity) that characterize the segments. The segmentation and/or index determination may be performed using, for example, the approach described in U.S. Pat. No. 9,064,320 entitled "Method and system for image analysis of selected tissue structures".

Density determiner 36 is configured to determine the density of the selected ROI using the attenuation of a second material (such as muscle tissue or other adjacent material, or a calibration phantom of known density) as a referent, again using the approach described in U.S. Pat. No. 9,064,320. The second material may be scanned by the same scanner to establish a formula for converting attenuation values to density values.

Processing then ends.

ROI Selection of Femoral Neck from Hip DXA Image

Figure 3:
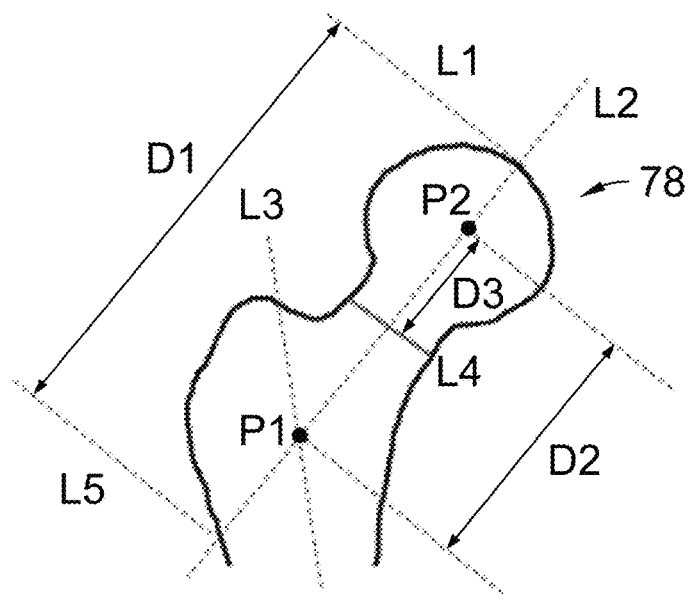
FIG. 3 illustrates morphometrics performed on a femur bone by the segmentation system of FIG. 1.

FIGS. 3 and 4A to 4F illustrate the application of system 10 to the selection of an ROI in the form of a femoral neck region from a hip DXA image. FIG. 3 illustrates the morphometrics performed on the femur bone. FIGS. 4A to 4F illustrate the intermediate results generated by system 10 at various steps of workflow 54.

As shown generally at 76 in FIG. 3, the tangent line (L1) of femoral head 78 is identified (after the femoral head and vertex point of the femoral head are recognized and identified during step 62); the neck axis (L2) is identified that is the central line across the femoral neck; the shaft axis (L3) is identified that is the central line across the shaft bone; the minimum cross sectional line (L4) is identified that is the shortest line parallel to L1 and transverse the femoral neck; the hip end line (L5) is identified that passes through the intersection point between L2 and shaft bone and is parallel to L1; the axis intersection point (P1) is identified that is the intersection of the neck axis (L2) and the shaft axis (L3); the femoral head central point (P2) is identified;

Based on the identified reference lines and points, the following morphometrics are measured by reference morphometric determiner 32: the hip axis length (D1) is calculated as the distance between L1 and L5; the distance between the axis intersection point (P1) and the femoral head central point (P2) is calculated as D2; the distance between the femoral head central point (P2) and the minimum cross-sectional line (L4) is calculated as D3.

Figure 4A:
FIGS. 4A to 4F illustrate intermediate results generated by the segmentation system of FIG. 1 at various steps of the workflow of FIG. 2.
Figure 4B:
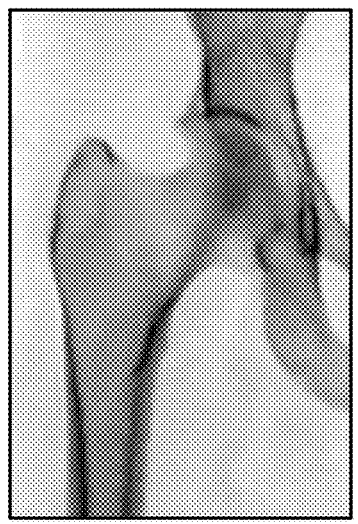
Figure 4C:
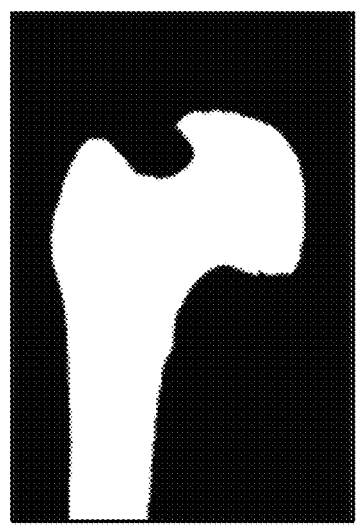

FIG. 4A is an original image 80 in the form of a hip DXA scan inputted into system 10 (cf. step 56); FIG. 4B is an inverted version 80' of image 80 (provided to assist naked-eye inspection and interpretation of FIG. 4A). FIG. 4C shows the result of the application of pre-trained (preferably deep learning) segmentation model 44 (cf. step 60) by segmenter 24 to segment the femur bone from the image, and to generate a segmented mask 82 of the segmented object (in this example, the femur bone).

Figure 4D:
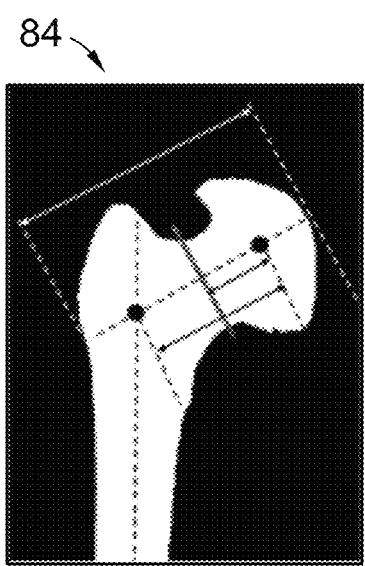
Figure 4E:
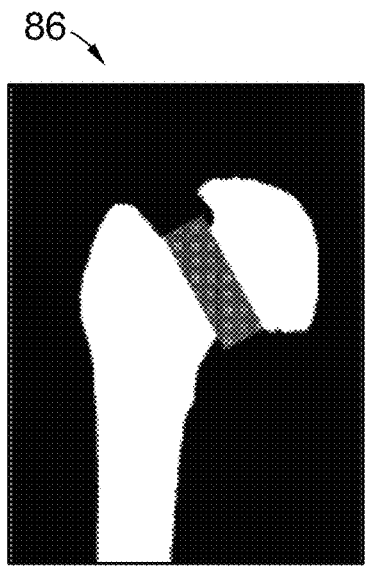

FIG. 4D shows the result of the morphometrics performed on the segmented femur bone (cf. step 66). FIG. 4E shows at 86 the result of the selection of the femoral neck ROI by ROI selector 34 (cf. steps 70 & 72). The minimum cross-sectional line (L4 in FIG. 3) is the central line of the region and the region width is selected as a percentage (in this example, 10%) of the hip axis length (cf. D1 in FIG. 3). (This percentage is configurable, and is stored in ROI selection settings 52.) The ROI selection may vary for different purposes or studies.

Figure 4F:
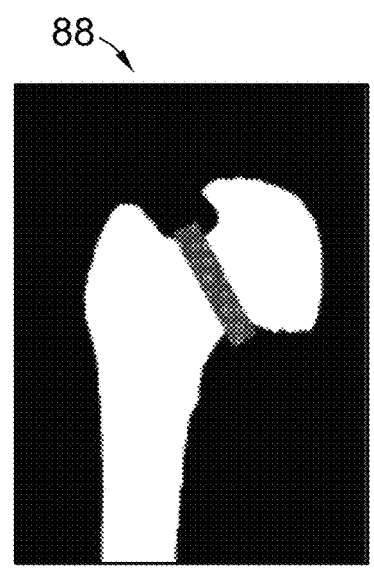

FIG. 4F shows at 88 the width of ROI selected to be 10% of D2 (cf. FIG. 3).

ROI Selection of Distal Radius from Wrist CT Image

Figure 5:
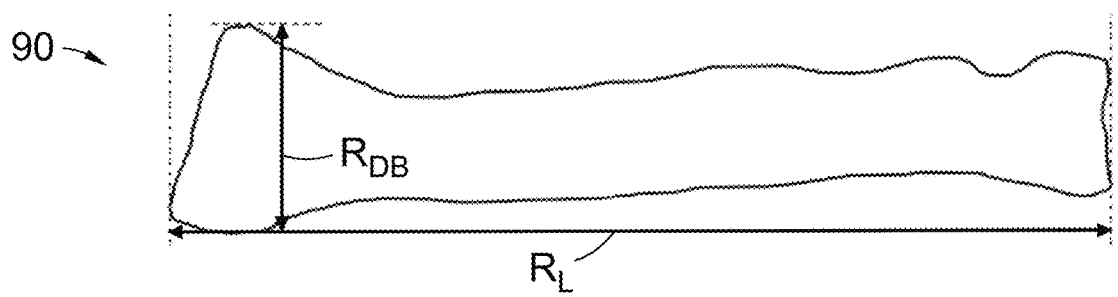
FIG. 5 illustrates morphometrics performed on a radius bone by the segmentation system of FIG. 1.
Figure 6A:
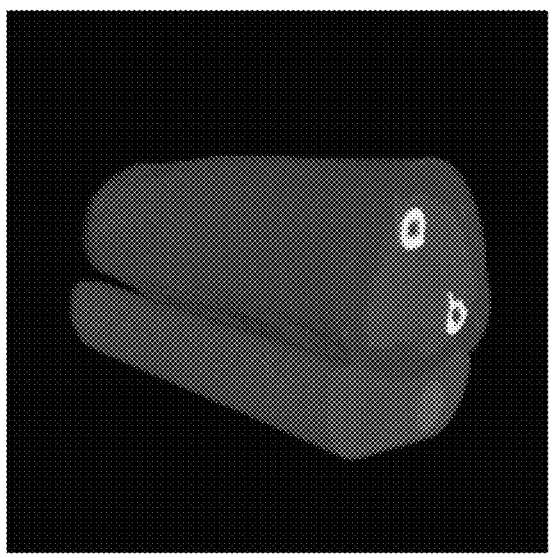
FIGS. 6A to 6N illustrate intermediate results generated by the segmentation system of FIG. 1 at various steps of the workflow of FIG. 2.
Figure 6B:
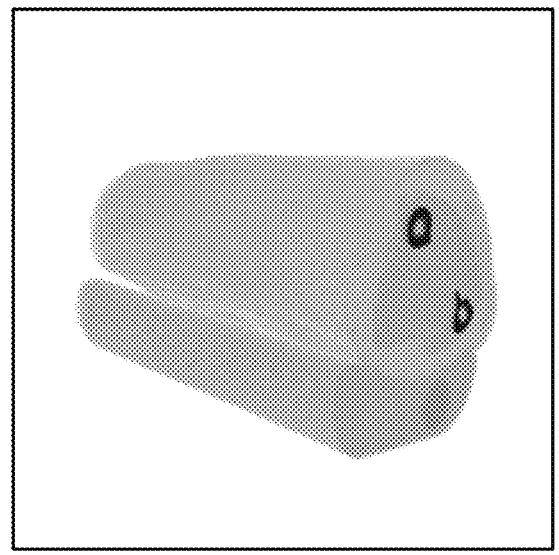
Figure 6C:
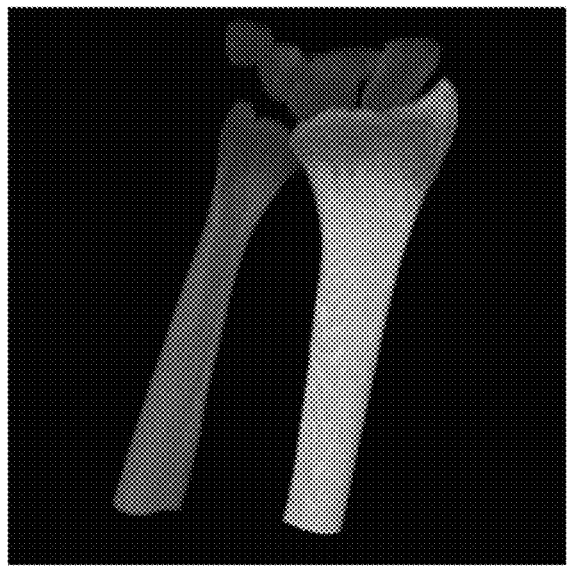
Figure 6D:
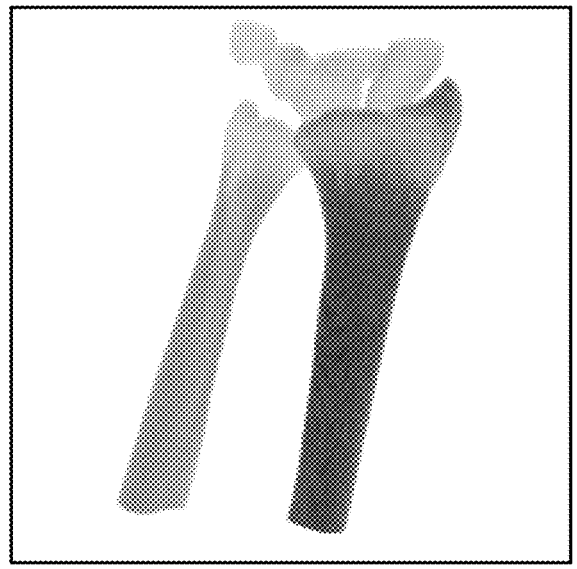
Figure 6E:
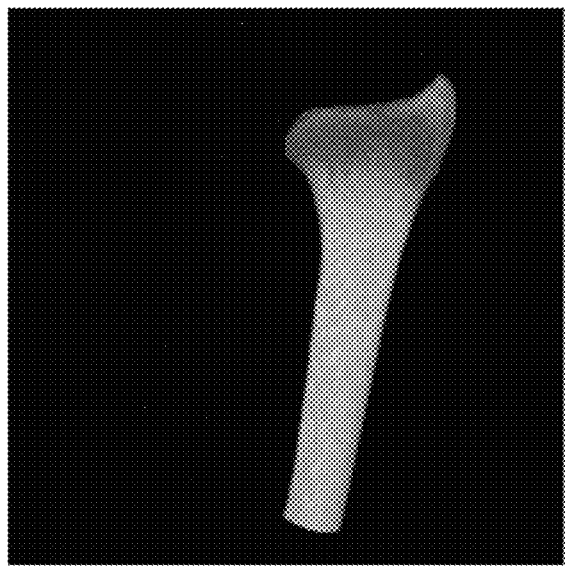
Figure 6F:
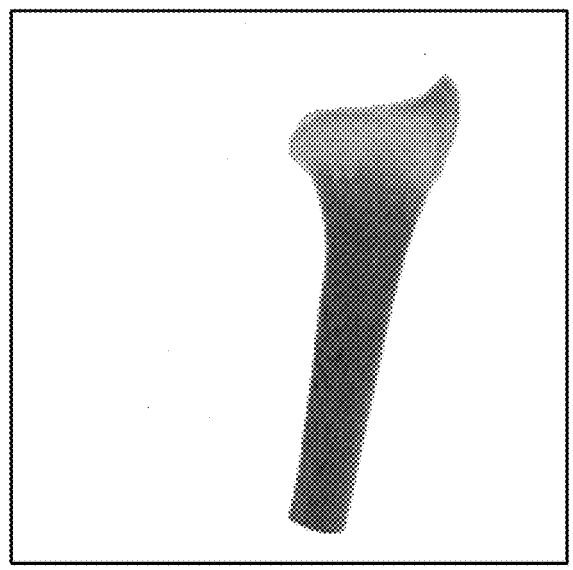
Figure 6G:
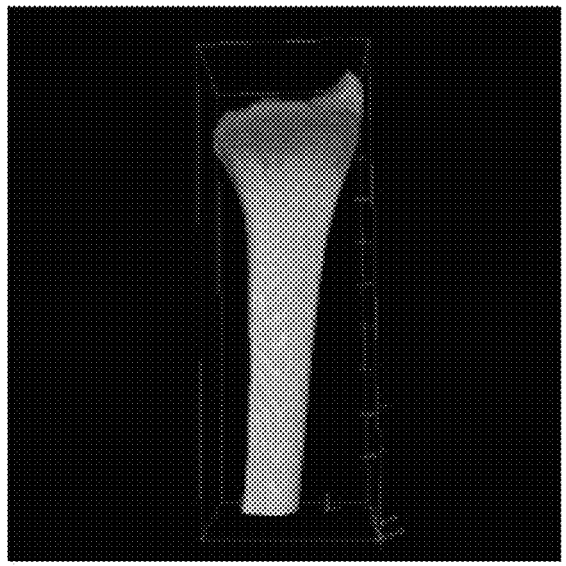
Figure 6H:
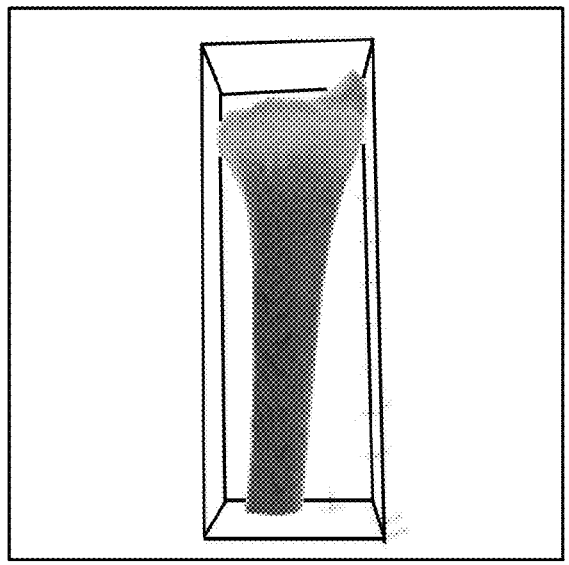
Figure 6I:
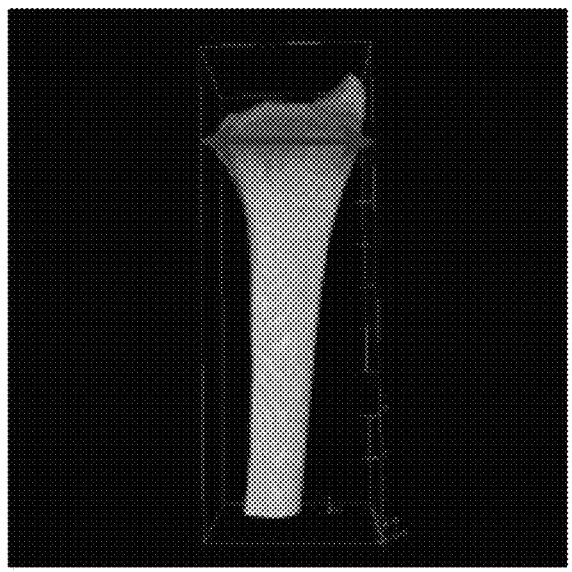
Figure 6J:
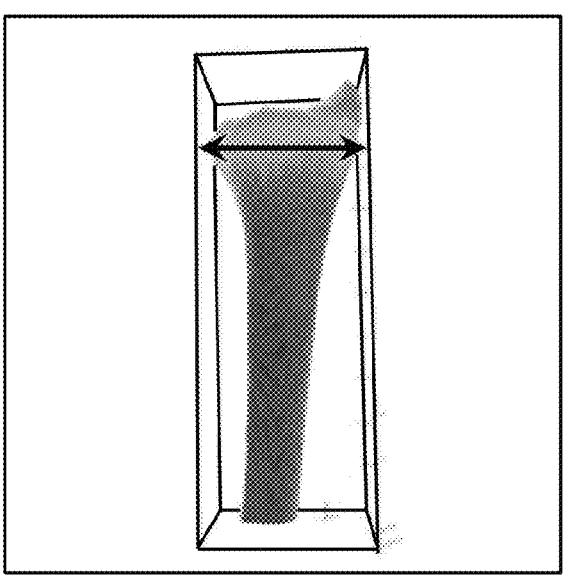
Figure 6K:
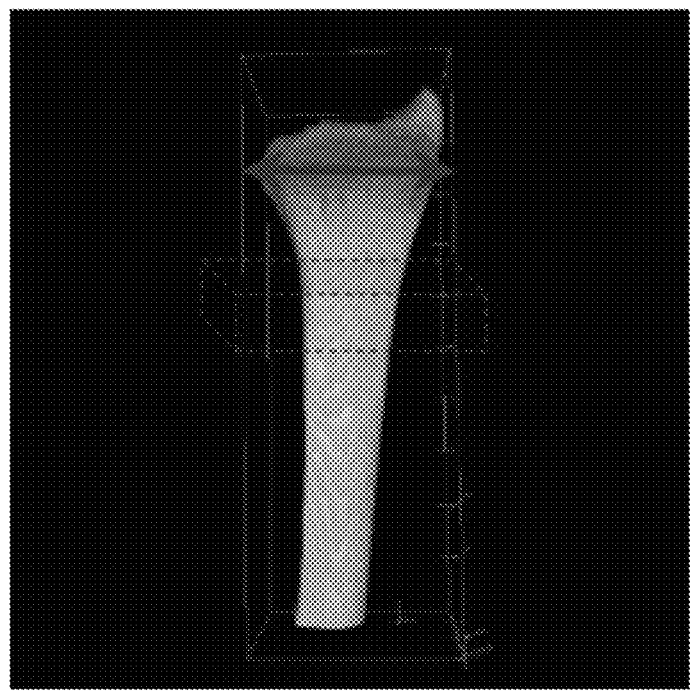
Figure 6L:
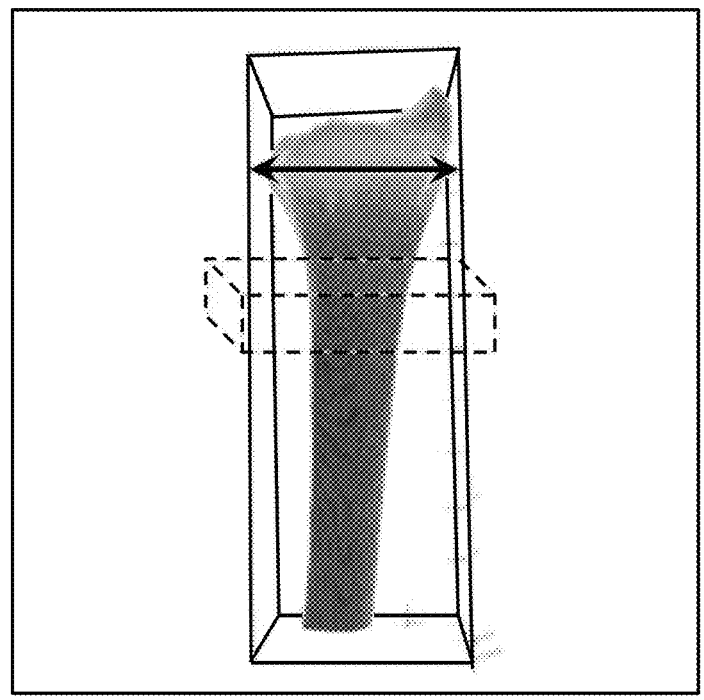
Figure 6M:
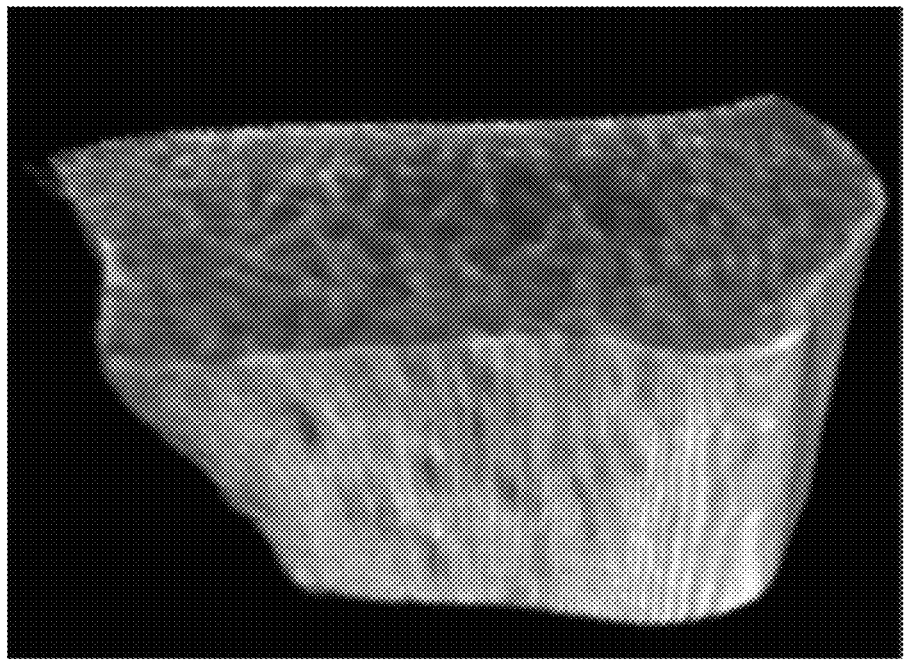
Figure 6N:
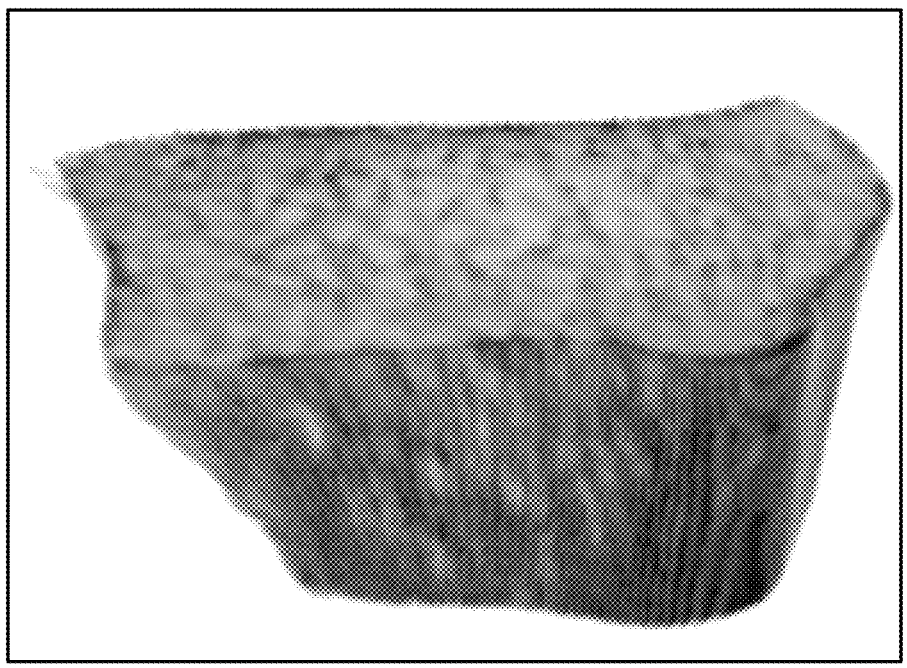

FIGS. 5 and 6A to 6N illustrate the application of system 10 in selecting an ROI, in the form of a distal radius region, from a wrist CT image. FIG. 5 illustrates morphometrics performed on a radius bone. FIGS. 6A to 6N illustrate the intermediate results generated at various steps of the ROI selection workflow 50. (FIGS. 6B, 6D, 6F, 6H, 6J, 6L and 6N are inverted versions of FIGS. 6A, 6C, 6E, 6G, 6I, 6K and 6M, respectively, and are again provided to assist naked-eye inspection and interpretation of FIGS. 6A, 6C, 6E, 6G, 6I, 6K and 6M.)

As shown at 90 in FIG. 5, radius distal breadth (ROB) is measured as the distance from the most medial point of the ulnar notch to the most lateral point of the styloid process; radius length ($R_L$) is measured as the distance from the most proximal end on the radial head to the tip of the styloid process.

FIG. 6A is an original image in the form of a wrist CT scan. FIG. 6C shows bones segmented by segmenter 24 (using pre-trained deep learning segmentation model 44) from the surrounding tissues (cf. step 60). FIG. 6E shows the radius bone as segmented by segmenter 24 (in this instance using a conventional connected component detection algorithm) from the other bones (cf. step 60). FIG. 6G shows the segmented radius bone, transformed by normalizer 28 from the image coordinates to the radius anatomy coordinates (cf. step 64). FIG. 6I shows the radius distal breadth (the double arrow line) is measured. FIG. 6K shows the region of interest (dash line box) is selected. The selected ROI starts at a distance of $R_{DB}$ from the tip of the distal radius. The height of the region is selected as half of $R_{DB}$. FIG. 6M is an image of the selected distal radius bone.

It will be understood to persons skilled in the art of the invention that many modifications may be made without departing from the scope of the invention, in particular it will be apparent that certain features of embodiments of the invention can be employed to form further embodiments.

It is to be understood that, if any prior art is referred to herein, such reference does not constitute an admission that the prior art forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

What is claimed is:

1. A computer-implemented method for analysing or monitoring a subject, the method comprising:
    identifying one or more objects of interest that have been segmented from a first image comprising any of a baseline scan, a follow-up scan or a reference image of the subject;
    identifying predefined landmarks of the objects;
    determining reference morphometries pertaining to the objects by performing morphometrics on the objects by reference to the landmarks, wherein determining the reference morphometries includes applying one or more image processing algorithms to the first image to calculate basic morphometries;
    selecting one or more regions of interest (ROIs) from the objects according to the reference morphometries, comprising identifying respective locations of the ROIs relative to the reference morphometries;
    performing a first analysis of the one or more ROIs;
    performing at least one corresponding second analysis of the one or more ROIs in respectively at least one second image comprising any other of a baseline scan, a follow-up scan or a reference image; generating a comparison of one or more results of the first analysis and one or more corresponding results of the second analysis; and
    outputting the comparison.

2. A method as claimed in claim 1, wherein each of the first and second analyses comprise a diagnostic, clinical or microstructure analysis.

3. A method as claimed in claim 1, comprising diagnosing or monitoring the subject including determining a density of one or more of the ROIs.

4. A method as claimed in claim 3, comprising determining the density of the one or more of the ROIs using attenuation of a referent material.

5. A method as claimed in claim 1, wherein the baseline scan, follow-up scan and/or reference image are derived from imaging modalities comprising one or more of CT, MR, DXA, ultrasound imaging and pathology imaging.

6. A method as claimed in claim 1, wherein the first image is baseline scan or reference image, and the second image is a follow-up scan.

7. A method as claimed in claim 1, comprising performing a plurality of corresponding second analyses of the one or more ROIs in a plurality of respective second images.

8. A method as claimed in claim 1, wherein the first image is baseline scan or reference image, and the method comprises (a) performing a plurality of corresponding second analyses of the one or more ROIs in a plurality of respective second images, and (b) generating comparisons of one or more results of the first analysis and the respective one or more results of the respective second analyses.

9. A method as claimed in claim 1, wherein performing determining the reference morphometries further includes applying one or more trained deep learning reference morphometric models to one or more of the basic morphometries to determine one or more of the reference morphometries.

10. A method as claimed in claim 1, wherein the comparison, when output, is usable to perform a diagnostic analysis, monitor a disease, or monitor a treatment.

11. A system for analysing or monitoring a subject, the system comprising:
    an object and landmark identifier configured to identify one or more objects of interest that have been segmented from a first image comprising any of a baseline scan, a follow-up scan or a reference image of the subject, and to identify predefined landmarks of the objects;
    a morphometer configured to determine reference morphometries pertaining to the objects by performing morphometrics on the objects by reference to the landmarks, wherein determining the reference morphometries includes applying one or more image processing algorithms to the first image to calculate basic morphometries; and
    a region selector configured to select one or more regions of interest (ROIs) from the objects according to the reference morphometries, comprising identifying respective locations of the ROIs and determining respective shapes and sizes of the ROIs relative to the reference morphometries;
    wherein the system is configured to:
    perform a first analysis of the one or more ROIs;
    perform at least one corresponding second analysis of the one or more ROIs in respectively at least one second image comprising any other of a baseline scan, a follow-up scan or a reference image;
    generate a comparison of one or more results of the first analysis and one or more corresponding results of the second analysis; and
    output the comparison.

12. A system as claimed in claim 11, wherein each of the first and second analyses comprise a diagnostic, clinical or microstructure analysis.

13. A system as claimed in claim 11, configured to diagnose or monitor the subject including determining a density of one or more of the ROIs.

14. A system as claimed in claim 13, configured to determine the density of the one or more of the ROIs using attenuation of a referent material.

15. A system as claimed in claim 11, wherein the baseline scan, follow-up scan and/or reference image are derived from imaging modalities comprising one or more of CT, MR, DXA, ultrasound imaging and pathology imaging.

16. A system as claimed in claim 11, wherein the first image is baseline scan or reference image, and the second image is a follow-up scan.

17. A system as claimed in claim 11, wherein the first image is baseline scan or reference image, and the system is configured to (a) perform a plurality of corresponding second analyses of the one or more ROIs in a plurality of respective second images, and (b) generate comparisons of one or more results of the first analysis and the respective one or more results of the respective second analyses.

18. A system as claimed in claim 11, wherein the comparison, when output, is usable to perform a diagnostic analysis, monitor a disease, or monitor a treatment.

19. A system as claimed in claim 11, wherein determining the reference morphometries further includes applying one or more trained deep learning reference morphometric models to one or more of the basic morphometries to determine one or more of the reference morphometries.

20. A non-transitory computer-readable medium, comprising a computer program that comprises program code configured to, when executed by one or more processors, implement the method of analysing or monitoring a subject of claim 1.

* * * * *